United States Patent
Lee et al.

(10) Patent No.: US 11,311,743 B2
(45) Date of Patent: Apr. 26, 2022

(54) ELECTRONIC DEVICE FOR SKIN MANAGEMENT OR SKIN TREATMENTS

(71) Applicant: LG Display Co., Ltd., Seoul (KR)

(72) Inventors: JungHyoung Lee, Daejeon (KR); Jaemin Moon, Seoul (KR); Jina You, Seoul (KR)

(73) Assignee: LG DISPLAY CO., LTD., Seoul (KR)

(*) Notice: Subject to any disclaimer, the term of this patent is extended or adjusted under 35 U.S.C. 154(b) by 0 days.

(21) Appl. No.: 16/727,378

(22) Filed: Dec. 26, 2019

(65) Prior Publication Data

US 2020/0391048 A1 Dec. 17, 2020

(30) Foreign Application Priority Data

Jun. 11, 2019 (KR) .................. 10-2019-0068821

(51) Int. Cl.
*H01L 51/50* (2006.01)
*A61N 5/06* (2006.01)
*H01L 51/52* (2006.01)

(52) U.S. Cl.
CPC ........ *A61N 5/0616* (2013.01); *H01L 51/5036* (2013.01); *H01L 51/5212* (2013.01); *H01L 51/5221* (2013.01); *H01L 51/5253* (2013.01); *A61N 2005/0647* (2013.01); *A61N 2005/0653* (2013.01); *A61N 2005/0659* (2013.01); *A61N 2005/0663* (2013.01); *A61N 2005/0666* (2013.01); *H01L 2251/533* (2013.01)

(58) Field of Classification Search
CPC .................. A61N 5/0616; H01L 2251/533
See application file for complete search history.

(56) References Cited

U.S. PATENT DOCUMENTS

| 2011/0248256 A1* | 10/2011 | Cok ................ H01L 27/322 257/40 |
| 2015/0028310 A1* | 1/2015 | Dai ............... H01L 27/3246 257/40 |
| 2016/0027862 A1 | 1/2016 | Lee et al. |
| 2016/0028036 A1* | 1/2016 | Xue ............... H01L 51/5036 257/40 |

(Continued)

FOREIGN PATENT DOCUMENTS

| CN | 107519583 A | 12/2017 |
| JP | 2015069758 A | 4/2015 |

(Continued)

OTHER PUBLICATIONS

Chinese Office Action dated Nov. 18, 2021 issued in corresponding Patent Application No. 201910763156.8 w/English Translation (17 pages).

*Primary Examiner* — Nathan J Jenness
*Assistant Examiner* — Skylar Lindsey Christianson
(74) *Attorney, Agent, or Firm* — Polsinelli PC

(57) ABSTRACT

An electronic device for skin management or skin treatments including an active area including a light emission area and a non-light emission area comprises a plurality of organic light emitting devices disposed in the light emission area and emitting same color light; and first to third wavelength converting layers overlapping the light emission area and a part of the non-light emission area, wherein light emitted from the plurality of organic light emitting devices is extracted to outside the electronic device through the first to third wavelength converting layers.

24 Claims, 13 Drawing Sheets

(56) References Cited

U.S. PATENT DOCUMENTS

2017/0246474 A1    8/2017  Schanze
2019/0366115 A1*  12/2019  Castel .................. A61N 5/0616

FOREIGN PATENT DOCUMENTS

| KR | 20170038951 A | 4/2017 |
|----|---------------|--------|
| WO | 2012017751 A  | 2/2012 |
| WO | 2016171207 A  | 10/2016 |

* cited by examiner

ELECTRONIC DEVICE FOR SKIN MANAGEMENT OR SKIN TREATMENTS

CROSS REFERENCE TO RELATED APPLICATION

This application claims priority from Korean Patent Application No. 10-2019-0068821 filed on Jun. 11, 2019, which is hereby incorporated by reference in its entirety.

BACKGROUND

Field of the Disclosure

The present disclosure relates to an electronic device for skin management or skin treatments.

Description of the Background

Skins may be damaged due to aging of cells, repetition of specific facial expressions, continued exposure to external environments (ultraviolet, fine dusts, and the like), stresses, and the like. For example, aging of cells and repetition of specific facial expressions may cause skin folds, and continued exposure to external environments, stresses, and the like may cause various troubles such as pimples and freckles.

An object of the management of skins for preventing or minimizing such damages in skins is to maintain clean and soft skins having no blemish, and, especially, skin management of faces among body parts has attracted the highest interest. Accordingly, people try to maintain clean skins by getting massages for skin management of faces, applying functional cosmetic products, and using various cleaning products.

Recently, devices that are attached to or worn by user's faces and output light (for example, a mask-type skin management device and the like) have appeared. In such light output devices, a plurality of light sources are disposed, and light can be output toward user's facial skins and the like.

However, development of such electronic devices is in an initial stage, and it is necessary to design the electronic devices in accordance with the necessities of various persons.

SUMMARY

An aspect of the present disclosure provides an electronic device for skin management or skin treatments emitting light of wavelengths from which effects of inflammation treatments and skin regeneration can be acquired.

Another aspect of the present disclosure provides an electronic device for skin management or skin treatments from which effects of inflammation treatments and skin regeneration can be acquired regardless of an ethnic group and a user's skin thickness.

Yet another aspect of the present disclosure provides an electronic device for skin management or skin treatments that includes a light source having a long life.

An electronic device for skin management or skin treatments according to an aspect of the present disclosure includes an active area including a light emission area and a non-light emission area. The electronic device comprises a plurality of organic light emitting devices disposed in the light emission area each for emitting the same color light and first to third wavelength converting layers overlapping with the light emission area and a part of the non-light emission area; wherein light emitted from the plurality of organic light emitting devices is extracted to the outside of the electronic device through the first to third wavelength converting layers.

The electronic device may further comprise a substrate. A first electrode of the organic light emitting devices may be disposed on the substrate, an organic layer of the organic light emitting devices may be disposed on the first electrode, a second electrode of the organic light emitting devices may be disposed on the organic layer and the first to third wavelength converting layers are disposed in the substrate.

The organic light emitting devices may be configured to emit green or blue color lights.

The electronic device may further comprise a partition wall disposed in the substrate and separating the first to third wavelength converting layers from each other.

The first electrode may contain a transparent conductive material, and the second electrode may contain a metal having reflectivity.

The organic layer may include at least a light emitting layer of one layer, and a wavelength of light emitted from the organic layer may be smaller than a wavelength converted by the first to third wavelength converting layers.

Light emitted through the first to third wavelength converting layers may have a wavelength of 600 nm to 850 nm.

Light emitted through the first to third wavelength converting layers may comprise light for penetrating into outer skin and inner skin of a user's skin and light for penetration into inner skin and lower skin of the user's skin.

The first wavelength converting layer, the second wavelength converting layer, and the third wavelength converting layer may convert light emitted from the organic layer into mutually-different wavelengths.

At least one of the first to third wavelength converting layers may convert light emitted from the organic light emitting device into light of an infrared wavelength band.

Each of the first wavelength converting layer, the second wavelength converting layer, and the third wavelength converting layer may include a resin layer and a plurality of wavelength converting particles dispersed in the resin layer.

A first groove, a second groove, and a third grove that overlap with the light emission area and a part of the non-light emission area and are separate from each other may be formed in one face of the substrate facing the first electrode, and the first wavelength converting layer may be disposed inside the first groove, the second wavelength converting layer may be disposed inside the second groove, and the third wavelength converting layer may be disposed inside the third groove.

The substrate may further include a fourth groove disposed between the first groove and the second groove, a fifth groove disposed between the second groove and the third groove, and a sixth groove disposed between the third groove and the first groove.

An area of each of the first to third grooves may be larger than an area of each of the fourth to sixth grooves.

A partition wall may be disposed inside the fourth to sixth grooves.

An upper face of the partition wall may be disposed at a position higher than upper faces of the first to third wavelength converting layers with respect to a position of the upper face of the substrate.

A refractive index of the partition wall may be lower than refractive indexes of the substrate and the first to third wavelength converting layers.

The electronic device may further comprises an auxiliary electrode that has a mesh shape and is disposed on the substrate, a part of the first electrode overlapping with the open area of the auxiliary electrode and a part of the first electrode connecting with the auxiliary electrode and including at least one open area in an area not overlapping with the auxiliary electrode; and an insulating film that overlaps with the auxiliary electrode, overlaps with a part of the first electrode, and is disposed to cover the open area of the first electrode.

In the active area, the non-light emission area may correspond to an area in which the insulating film is disposed, and the light emission area may correspond to an area in which the insulating film is not disposed.

The resistivity of the first electrode may be higher than the resistivity of the auxiliary electrode The partition wall may overlap the insulating film.

The substrate may have one face in which a plurality of protrusions are integrally formed, and the first to third wavelength converting layers may be formed in the other face of the substrate opposite the one face and facing the first electrode.

The substrate may have a minimum thickness between the protrusion and another protrusion adjacent to the protrusion, and at least one area in which the substrate has the minimum thickness may overlap the insulating film and the partition wall.

The electronic device according may further include an encapsulation member disposed on the second electrode, wherein the encapsulation member may include: a capping layer disposed to cover the second electrode; an encapsulation layer disposed to cover the capping layer; an adhesion layer disposed on the substrate on which the encapsulation layer is disposed; and a metal film disposed on the adhesion layer.

According to aspects of the present disclosure, an electronic device emitting light of wavelengths from which effects of inflammation treatments and skin regeneration can be acquired can be provided.

According to aspects of the present disclosure, an electronic device from which effects of inflammation treatments and skin regeneration can be acquired regardless of an ethnic group and a user's skin thickness can be provided.

According to aspects of the present disclosure, an electronic device for skin management or skin treatments that includes a light source having a long life can be provided.

BRIEF DESCRIPTION OF THE DRAWINGS

The accompanying drawings, which are included to provide a further understanding of the disclosure and are incorporated in and constitute a part of the disclosure, illustrate aspects of the disclosure and together with the description serve to explain the principle of the disclosure.

In the drawings.

DETAILED DESCRIPTION

Figure 1:
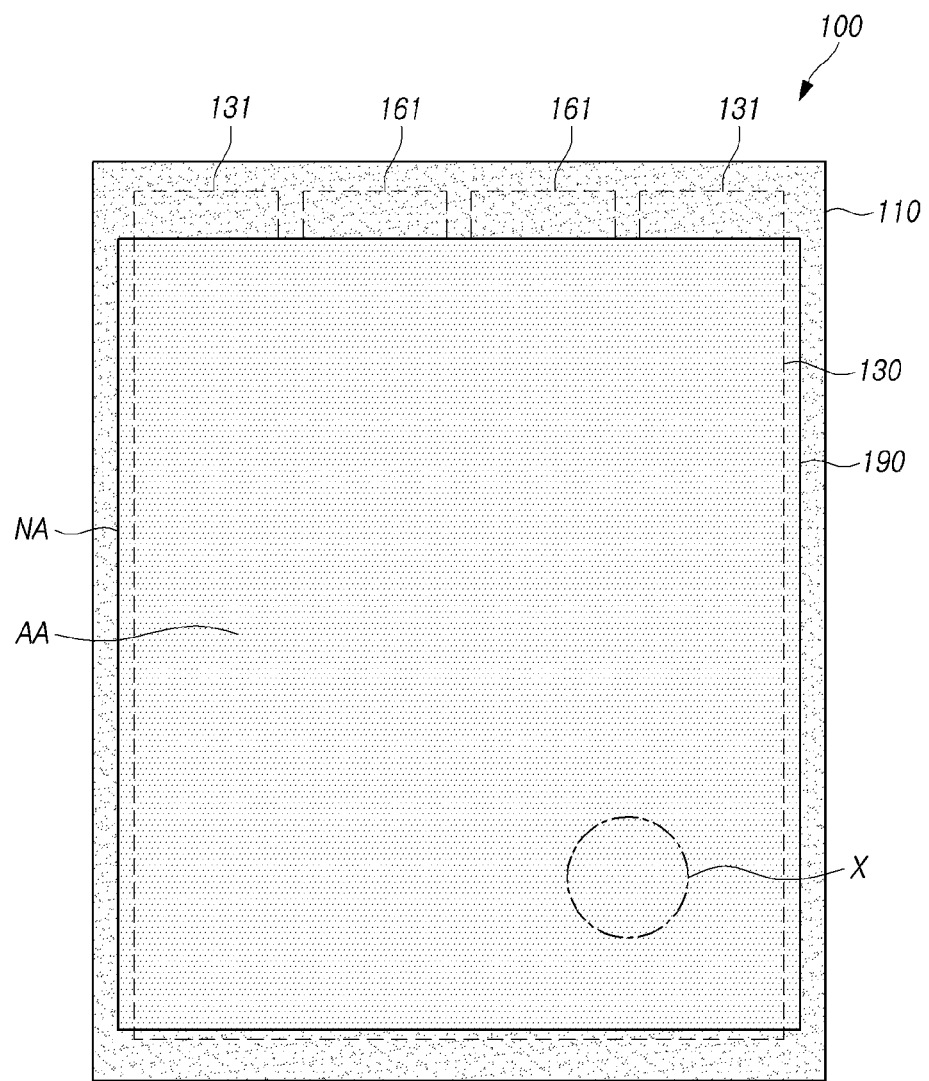
FIG. 1 is a plan view schematically illustrating an electronic device according to an aspect of the present disclosure.

Advantages and features of the present disclosure and methods for achieving those will become more apparent by referring to exemplary aspects described later in detail with reference to the attached drawings. However, the present disclosure is not limited to the aspects disclosed below and will be embodied in various different forms, and the aspects are provided for allowing the disclosure of the present disclosure to be complete and completely informing a person skilled in the art of the scope of the disclosure, and the present disclosure is defined only by the claims.

In addition, shapes, sizes, ratios, angles, the number, and the like disclosed in the drawings for describing the aspects of the present disclosure are examples, and the present disclosure is not limited to the illustrations. Like reference numerals denote like elements over the entire specification. In addition, in describing the present disclosure, in a case in which a specific description of a relating known technology may unnecessarily causes the gist of the present disclosure to be unclear, detailed description thereof will be omitted. In a case in which "including", "having", "formed", and the like are used in this specification, unless "only" is used, other parts may be added. In a case in which a constituent element is represented in a single form, unless otherwise mentioned, it may include a case in which a plurality thereof is included.

In addition, in the interpretation of constituent elements of aspects of the present disclosure, it should be understood an error range is included although there is no explicit description thereof.

Hereinafter, some aspects of the present disclosure will be described in detail with reference to the accompanying illustrative drawings. In designating elements of the drawings by reference numerals, the same elements will be designated by the same reference numerals although they are shown in different drawings. Further, in the following description of the present disclosure, a detailed description of known functions and configurations incorporated herein will be omitted when it may make the subject matter of the present disclosure rather unclear.

In addition, terms, such as first, second, A, B, (a), (b) or the like may be used herein when describing components of the present disclosure. Each of these terminologies is not used to define an essence, order or sequence of a corresponding component but used merely to distinguish the corresponding component from other component(s). In the case that it is described that a certain structural element "is connected to", "is coupled to", or "is in contact with" another structural element, it should be interpreted that another structural element may "be connected to", "be coupled to", or "be in contact with" the structural elements as well as that the certain structural element is directly connected to or is in direct contact with another structural element.

Figure 2:
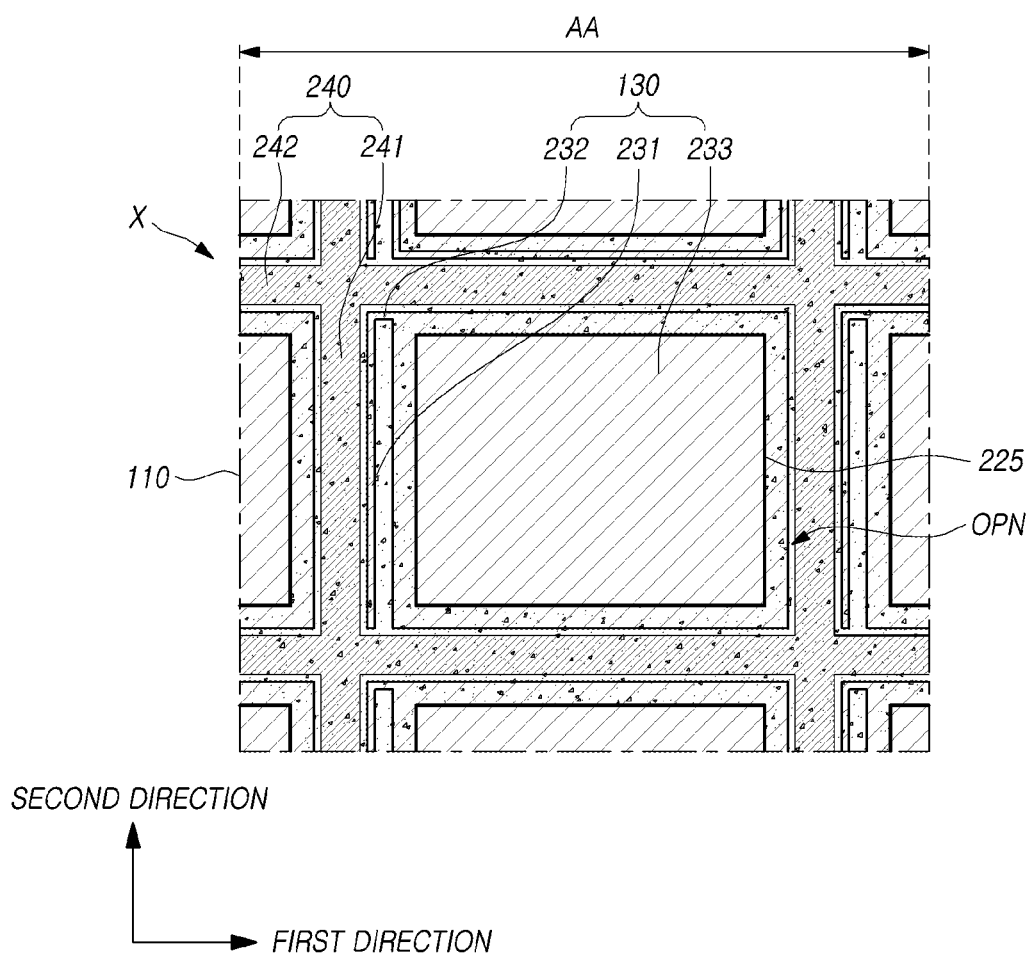
FIG. 2 is a specific plan view of an area X illustrated in FIG. 1.

FIG. 1 is a plan view schematically illustrating an electronic device according to an aspect of the present disclosure. FIG. 2 is a specific plan view of an area X illustrated in FIG. 1.

Referring to FIGS. 1 and 2, an electronic device 100 according to an aspect of the present disclosure may include an active area AA in which a plurality of organic light emitting devices OLED are disposed and a non-active area NA disposed on an outer side of the active area AA.

As illustrated in FIG. 1, the non-active area NA may include a plurality of pad electrodes 131 and 161.

A first electrode 130 of an organic light emitting device OLED disposed in the active area AA extends to the non-active area NA and can perform the role of a pad electrode 131, and a second electrode of the organic light emitting device OLED also extends to the non-active area NA and can perform the role of a pad electrode 161. However, the present disclosure is not limited thereto.

For example, an auxiliary electrode 240 illustrated in FIG. 2 extends to the non-active area NA and can perform the role of a pad electrode, and pad electrodes extending from the auxiliary electrode 240, the first electrode 130, and the second electrode may be disposed in an overlapping manner.

A plurality of pad electrodes 131 and 161 disposed in the non-active area NA may be electrically connected to the outside. A signal (for example, a DC voltage) may be applied to the organic light emitting device OLED disposed in the active area AA through the non-active area NA.

In accordance with application of a signal to the organic light emitting device OLED, the organic light emitting device OLED emits light, and accordingly, light can be output to the outside of the electronic device 100 through the active area AA.

In addition, an encapsulation member 190 that can prevent penetration of moisture and a foreign material may be disposed on the organic light emitting device OLED.

The encapsulation member 190 may be disposed in the active area AA and the non-active area NA.

In description presented below, for the convenience of description, the structure of the active area AA of the electronic device 100 according to the present disclosure will be focused on.

As illustrated in FIG. 2, the electronic device 100 according to an aspect of the present disclosure includes an auxiliary electrode 240 overlapping with the first electrode 130 of the organic light emitting device OLED.

Referring to FIG. 2, the auxiliary electrode 240 may be disposed on a substrate 110.

The auxiliary electrode 240 may be in a matrix shape or a mesh shape having a thin width in the entire active area AA. In a case in which the auxiliary electrode 240 is disposed in the mesh shape, an open area of the auxiliary electrode 240 is disposed in a hexagonal shape, an octagonal shape, a circular shape, or the like, and a uniform current is applied to the first electrode 130 of the entire active area AA, and accordingly, light emission having uniform luminance can be performed by the electronic device 100 having a large area.

The auxiliary electrode 240 may include a plurality of first auxiliary electrodes 241 extending in a first direction and a plurality of second auxiliary electrodes 242 extending in a second direction that is a direction intersecting with the first direction.

Such an auxiliary electrode 240 may include at least one open area OPN in the active area AA.

For example, two first auxiliary electrodes 241 and two second auxiliary electrodes 242 intersect with each other, whereby one open area OPN may be formed.

A part of the first electrode 130 of the organic light emitting device OLED may overlap with the open area OPN formed by the auxiliary electrode 240. A part of the first electrode 130 may be electrically connected to the auxiliary electrode 240.

The first electrode 130 may include a first part 231 that is electrically connected to the auxiliary electrode 240, a second part 232 that is connected to the first part 231 and extends in a direction different from a direction in which the first part 231 extends, and a third part 233 that is connected to the second part 232 and has a plate shape.

More specifically, the second part 232 may be an area that is connected to the third part 233 and extends from the third part 233 in the first direction, and the first part 231 may be an area that extends from the second part 232 in the second direction.

However, the structure of the electronic device 100 according to an aspect of the present disclosure is not limited thereto. For example, there may be one or three or more parts that branch from the third part 233 of the first electrode 130 and is connected to the auxiliary electrode 240.

An insulating film 225 that overlaps with the auxiliary electrode 240 and overlaps a part of the first electrode 130 may be disposed.

Here, the insulating film 225 may be composed of an inorganic material such as SiOx or SiNx. However, the present disclosure is not limited thereto, and the insulating film 225 may be composed of an organic material such as a photo-acryl or may be composed of a plurality of layers of an inorganic material and an organic material.

The insulating film 225 may be arranged to overlap with a part of the open area OPN arranged by the auxiliary electrode 240 while overlapping with the auxiliary electrode 240. Here, the insulating film 225 may overlap with the first part 231 and the second part 232 of the first electrode 130, and, together with this, the insulating film 225 may overlap with a part of the third part 233 of the first electrode 130.

In another aspect, the insulating film 225 may not overlap with a part of the third part 233.

In this way, while the insulating film 225 disposed in the active area AA is configured to cover the auxiliary electrode 240 and the first electrode 130 disposed on the auxiliary electrode 240, the insulating film 225 is not disposed in a light emission area in which light of the organic light emitting device OLED is emitted.

Particularly, the insulating film 225 of the active area AA is formed to surround the auxiliary electrode 240 and decreases a level difference according to the auxiliary electrode 240, whereby components formed thereafter can be stably formed without being open-circuited.

An organic layer and the second electrode of the organic light emitting device OLED may be sequentially disposed on the substrate 110 in which such an insulating film 225 is disposed. The organic layer may include an area overlapping with the auxiliary electrode 240, the first electrode 130, the insulating film 225, and the second electrode.

The active area AA of the electronic device 100 according to an aspect of the present disclosure having such a planar structure may include a plurality of light emission areas and a plurality of non-light emission areas.

For example, the active area AA may include a light emission area. The light emission area may be an area not overlapping with the insulating film 225.

The active area AA may include a non-light emission area. The non-light emission area may be an area corresponding to an area in which the insulating film 225 is disposed.

The structure of the active area AA of the electronic device 100 according to an aspect of the present disclosure will be reviewed as below with reference to FIG. 3.

Figure 3:
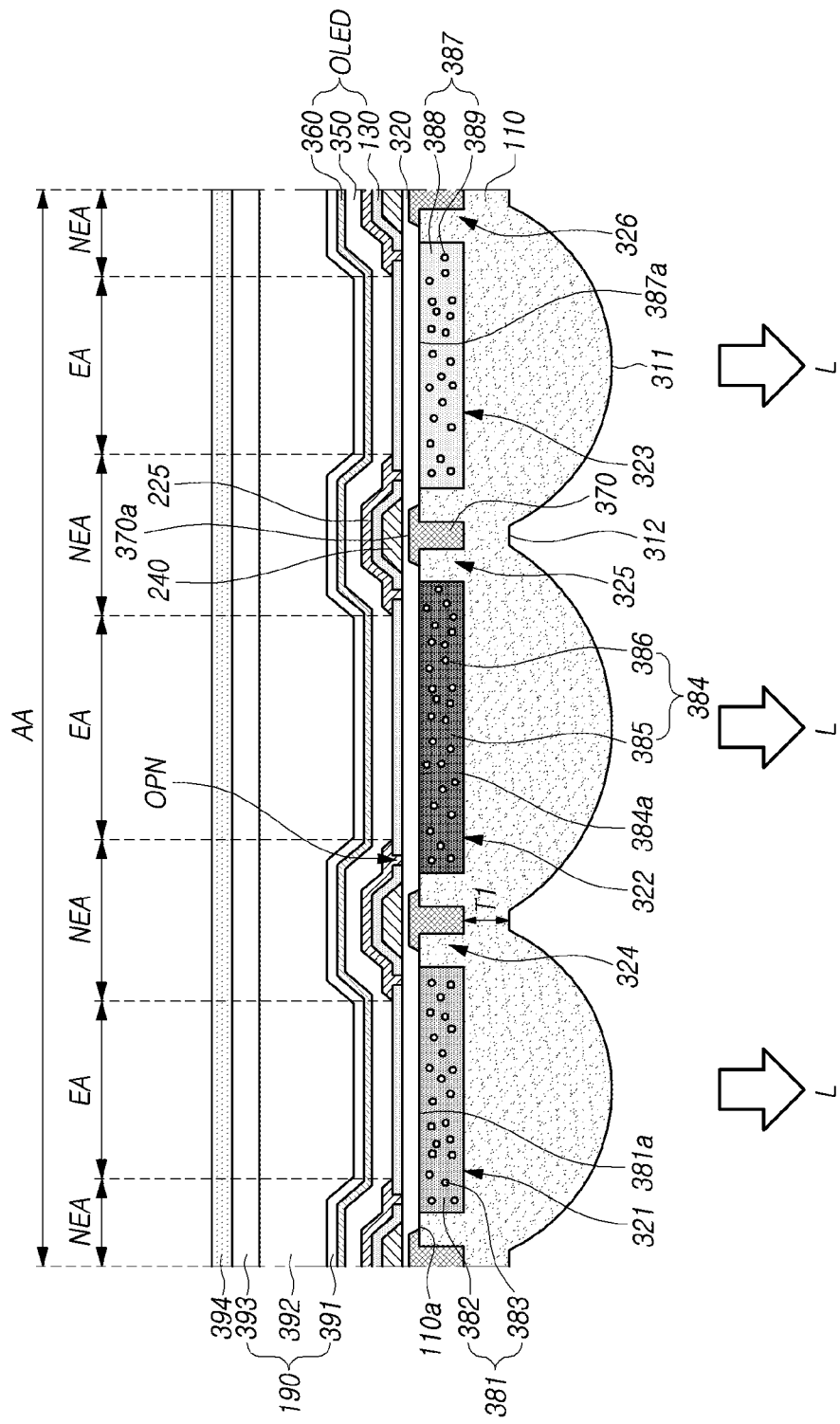
FIG. 3 is a cross-sectional view of the area X illustrated in FIG. 1.

FIG. 3 is a cross-sectional view of the area X illustrated in FIG. 1.

Referring to FIG. 3, the electronic device 100 according to an aspect of the present disclosure may include a substrate 110 having a rear face on which a plurality of protrusions 311 is integrally formed. Such a substrate 110 may include a first wavelength converting layer 381, a second wavelength converting layer 384, and a third wavelength converting layer 387 through which light L emitted from an organic light emitting device OLED passes before output to the outside of the electronic device 100.

In addition, the electronic device 100 may include an organic light emitting device OLED disposed on the substrate 110.

The electronic device 100 according to an aspect of the present disclosure may be a lighting apparatus including an organic light emitting device OLED. For example, the electronic device 100 may be a cosmetic device or a treatment device including an organic light emitting device OLED.

The substrate 110 may be composed of a flexible material having high transmittance. Accordingly, the electronic device 100 according to an aspect of the present disclosure can be bent or folded.

For example, the substrate 110 may be in the form of a film containing one selected from a group composed of a polyester-based polymer, a silicon-base polymer, an acryl-based polymer, a polyolefin-based polymer, and a copolymer thereof. More specifically, the substrate 110 may contain one selected from a group composed of PET, PBT, polysilane, polysiloxane, polysilazane, polycarbosilane, polyacrylate, polymethacrylate, polymethylacrylate, polymethylmetacrylate, polyethylacrylate, polyethylmetacrylate, COC, COP, PE, PP, PI, PMMA, PS, POM, PEEK, PES, PTFE, PVC, PC, PVDF, PFA, SAN, and a combination thereof.

A buffer layer 320 may be disposed on such a substrate 110.

Although the buffer layer 320 is illustrated to have a configuration of a single layer in FIG. 3, the present disclosure is not limited thereto. For example, the buffer layer 320 may be multiple-buffer layer composed of multiple layers.

The buffer layer 320 may contain an inorganic insulating material. For example, the buffer layer 320 may contain any one of SiOx, SiNx, and SiON. However, the present disclosure is not limited thereto.

A plurality of auxiliary electrodes 240 may be disposed on the buffer layer 320. Although a configuration in which the auxiliary electrode 240 is a single layer is illustrated in FIG. 3, the present disclosure is not limited thereto, and the auxiliary electrode 240 may be multiple layers.

The first electrode 130 of the organic light emitting device OLED may be disposed on the auxiliary electrode 240.

A part of the first electrode 130 may be brought into contact with the auxiliary electrode 240.

The first electrode 130 may contain a material having electric resistance higher than that of the auxiliary electrode 240.

For example, the auxiliary electrode 240 may contain any one of aluminum (Al), gold (Au), copper (Cu), titanium (Ti), tungsten (W), and molybdenum (Mo), and an alloy thereof. The first electrode 130 may include a transparent conductive material, for example, any one of indium tin oxide (ITO), indium zinc oxide (IZO), and indium gallium zinc oxide (IGZO).

The first electrode 130 is formed using a transparent conductive material and has an advantage of transmitting emitted light and has a disadvantage of having electric resistance higher than that of a non-transparent metal.

Accordingly, a distribution of currents applied to the active area becomes uneven due to high resistance of the transparent conductive material, and such a non-uniform current distribution inhibits uniform-luminance light emission of the electronic device 100.

In the present disclosure, by disposing the auxiliary electrode 240 in the entire active area AA, a uniform current is applied to the first electrode 130 of the organic light emitting device OLED disposed in the active area AA, and there is an effect of uniform luminance of the active area AA of the electronic device 100 having a large area for each position.

In addition, in a case in which a foreign material is inserted into at least one organic light emitting device OLED among a plurality of organic light emitting devices OLED disposed in the active area AA, a voltage is concentrated on the first electrode 130 present at a position at which the foreign material is inserted, and voltages applied to the other organic light emitting devices OLED disposed in the active area AA become lower than a drive voltage, and light emission of the organic light emitting devices OLED disposed in the active area AA may not be achieved.

However, a short reduction effect of the lighting apparatus LD can be acquired through the structure of the first electrode 130 according to an aspect of the present disclosure.

More specifically, as illustrated in FIG. 3, the first electrode 130 of the organic light emitting device OLED disposed in the active area AA may be brought into contact with the auxiliary electrode 240. As described above, since the resistivity of the first electrode 130 is higher than the resistivity of the auxiliary electrode 240, the first electrode 130 connected to the auxiliary electrode 240 may operate as a resistance component.

Accordingly, even in a case in which a foreign material is inserted into at least one organic light emitting device OLED among the plurality of organic light emitting devices OLED disposed in the active area AA, and a voltage is concentrated on the first electrode 130 that is present at a position at which the foreign material is inserted, the voltage is not different much from voltages applied to the other organic light emitting devices (OLED) disposed in the active area AA, and organic light emitting devices (OLED) into which a foreign material has not been inserted can emit light regardless of the organic light emitting device (OLED) into which the foreign material has been inserted.

The organic light emitting device OLED disposed in an area in which a foreign material is present has high electric resistance due to the foreign material, and a current applied to the organic light emitting device OLED decreases much, whereby the organic light emitting device OLED may not emit light.

To sum up, in the present disclosure, as illustrated in FIG. 3, by bringing the first electrode 130 of the organic light emitting device OLED and the auxiliary electrode 240 into contact with each other, only the organic light emitting device OLED disposed in the area in which the foreign material is present does not emit light, and there is an advantage of improving the life of the lighting apparatus.

An insulating film 225 overlapping with the auxiliary electrode 240 may be disposed on the first electrode 130 of the organic light emitting device OLED having such a structure.

An open area OPN may be formed in an area in which the first electrode 130 and the auxiliary electrode 240 do not overlap with each other. The insulating film 225 may be disposed in the open area OPN.

The insulating film 225 is formed to surround the auxiliary electrode 240 and decreases a level difference according to the auxiliary electrode 240, whereby components formed thereafter can be stably formed without being open-circuited.

In the active area AA, an organic layer 350 may be disposed on the substrate 110 on which the insulating film 225 is disposed.

The organic layer 350 may be disposed to cover the insulating film 225.

Although not illustrated in FIG. 3, the organic layer 350 may have a multi-layer structure and may include at least a light emitting layer of one layer.

The second electrode 360 of the organic light emitting device OLED may be disposed to cover the organic layer 350.

Such a second electrode 360 may contain a metal having reflectivity.

For example, the second electrode 360 may contain a metal such as aluminum (Al), molybdenum (Mo), copper (Cu), or silver (Ag) or an alloy such as molybdenum titanium (MoTi). However, the present disclosure is not limited thereto.

The organic layer 350 and the second electrode 360 may be arranged over the entire face of the active area AA.

The electronic device 100 according to an aspect of the present disclosure may be a bottom emission type in which light generated from the organic layer 350 is emitted toward a substrate 110 direction.

An encapsulation member 390 that can prevent penetration of moisture and a foreign material into the organic light emitting device OLED may be disposed on the second electrode 360.

The encapsulation member 390 may include a capping layer 391, an encapsulation layer 392, an adhesion layer 393, and a metal film 394.

The capping layer 391 may be disposed on the second electrode 360 of the organic light emitting device OLED. The capping layer 391 may be disposed to cover the second electrode 360.

The capping layer 391 is a component for performing the role of protecting the second electrode 360 of the organic light emitting device OLED and may be configured as a single layer composed of an organic material. However, the present disclosure is not limited thereto. For example, the capping layer 391 may contain an inorganic material and may be composed of multiple layers.

The encapsulation layer 392 may be disposed on the capping layer 391. The encapsulation layer 392 may be disposed to cover the capping layer 391.

Such an encapsulation layer 392 may be composed of an inorganic material such as SiOx or SiNx. However, the present disclosure is not limited thereto. In addition, although a configuration in which the encapsulation layer 392 is a single layer is illustrated in FIG. 3, the encapsulation layer 392 may be composed of multiple layers. In such a case, the encapsulation layer 392 may have a configuration in which an inorganic film and an organic film are alternately disposed. However, the present disclosure is not limited thereto.

The adhesion layer 393 may be disposed on the encapsulation layer 392. The adhesion layer 393 may be disposed to cover the encapsulation layer 392. In addition, the adhesion layer 393 may further contain a moisture absorbent and the like.

The metal film 394 may be disposed on the adhesion layer 393.

The adhesion layer 393 has the role of bonding the metal film 394 disposed on the adhesion layer 393 to the substrate 110 in which the encapsulation layer 392 is disposed and can prevent penetration of moisture or a foreign material into the organic light emitting device OLED.

The electronic device 100 may include a light emission area EA and a non-light emission area NEA in the active area AA.

The light emission area EA may be an area corresponding to an area not overlapping with the insulating film 225. The non-light emission area NEA may be an area corresponding to an area in which the insulating film 225 is disposed.

A plurality of grooves may be formed on one face of the substrate 110. For example, the one face of the substrate 110 in which the plurality of grooves are formed may be one face opposite the face on which a plurality of protrusions 311 are formed.

In another aspect, one face of the substrate 110 in which a plurality of grooves are formed may be a face brought into contact with the rear face of the buffer layer 320.

The substrate 110 may include a first groove 321, a second groove 322, and a third groove 323 that are disposed to be separate from each other.

The first wavelength converting layer 381 may be disposed in the first groove 321, the second wavelength converting layer 384 may be disposed in the second groove 322, and the third wavelength converting layer 387 may be disposed in the third groove 323.

A part of each of the first to third wavelength converting layers 381, 384, and 387 may overlap with the light emission area EA.

On the other hand, the remaining part of each of the first to third wavelength converting layers 381, 382, and 384 may also overlap with a part of the non-light emission area NEA.

In the electronic device 100 according to an aspect of the present disclosure, light L emitted from the organic light emitting device OLED is directed toward the substrate 110 direction. Even in a case in which such light is directed in various directions, the first to third wavelength converting layers 381, 384, and 387 overlap with the light emission area EA and overlap with a part of the non-light emission area NEA, and accordingly, the light L emitted from the organic light emitting device OLED can be extracted to the outside of the substrate 110 through the first to third wavelength converting layers 381, 384, and 387.

The first to third wavelength converting layers 381, 384, and 387 can perform the role of converting the wavelength of the light emitted from the organic light emitting device OLED.

According to the present disclosure, the plurality of organic light emitting devices disposed in the light emission area each are configured to emit the same color light. The light L emitted from the organic light emitting device OLED may be blue light or green light. However, the present disclosure is not limited thereto. The light L extracted to the outside of the electronic device 100 through the first to third wavelength converting layers 381, 384, and 387 may have a wavelength of 600 nm to 850 nm.

A wavelength at which a maximum peak of light that has passed through the first wavelength converting layer 381 appears may be shorter than a wavelength at which a maximum peak of light that has passed through the second wavelength converting layer 384 or the third wavelength converting layer 387 appears.

A wavelength at which a maximum peak of light that has passed through the second wavelength converting layer 384 appears may be shorter than a wavelength at which a maximum peak of light that has passed through the third wavelength converting layer 387 appears.

For example, the light that has passed through the first wavelength converting layer 381 has a wavelength of 600 nm to 680 nm, and a wavelength at which the maximum peak thereof appears may be 630 nm. However, the present disclosure is not limited thereto.

The light that has passed through the second wavelength converting layer 384 has a wavelength that is longer than 680 nm and is equal to or shorter than 780 nm, and a wavelength at which a maximum peak thereof appears may be 730 nm. However, the present disclosure is not limited thereto.

The light that has passed through the third wavelength converting layer 387 has a wavelength that is longer than 780 nm and is equal to or shorter than 850 nm, and a wavelength at which a maximum peak thereof appears may be 830 nm. However, the present disclosure is not limited thereto.

To sum up, the light that has passed through the first wavelength converting layer 381 may be red light, and the light that has passed through the second wavelength converting layer 384 may also be red light that is red light having a wavelength longer than that of the light that has passed through the first wavelength converting layer 381. In addition, the light that has passed through the third wavelength converting layer 387 may be infrared light.

Each of the first to third wavelength converting layers 381, 384, and 387 may have a composition in which a plurality of wavelength converting particles 383, 386, and 389 are respectively dispersed in resin layers 382, 385, and 388.

More specifically, the first wavelength converting layer 381 may have a composition in which a plurality of first wavelength converting particles 383 are dispersed in a first resin layer 382. Here, the plurality of first wavelength converting particles 383 can convert the wavelength of light L emitted from the organic light emitting device OLED into light having a wavelength of 600 nm to 680 nm. However, the present disclosure is not limited thereto.

The second wavelength converting layer 384 may have a composition in which a plurality of second wavelength converting particles 386 are dispersed in a second resin layer 385. Here, the plurality of second wavelength converting particles 386 can convert the wavelength of light L emitted from the organic light emitting device OLED into light having a wavelength that is longer than 680 nm and is equal to or shorter than 780 nm. However, the present disclosure is not limited thereto.

The third wavelength converting layer 387 may have a composition in which a plurality of third wavelength converting particles 389 is dispersed in a third resin layer 388. Here, the plurality of third wavelength converting particles 389 can convert the wavelength of light L emitted from the organic light emitting device OLED into light having a wavelength that is longer than 780 nm and is equal to or shorter than 850 nm. However, the present disclosure is not limited thereto.

The first to third wavelength converting particles 383, 386, and 389 may be quantum dots.

For example, each of the first to third wavelength converting particles 383, 386, and 389 may be independently selected from a group composed of CdS, CdSe, CdTe, ZnS, ZnSe, ZnTe, ZnO, CdSeS, CdSeTe, CdSTe, ZnSeS, ZnSeTe, ZnSTe, CdZnS, CdZnSe, CdZnTe, CdZnSeS, CdZnSeTe, CdZnSTe, GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, InAlPAs, CdSe—ZnS, InP—ZnS, and combinations thereof. However, the present disclosure is not limited thereto.

As the first to third wavelength converting particles 383, 386, and 389 different materials may be selected, and sizes of particles may be different from each other.

As described above, the light L emitted from the organic light emitting device OLED may be blue light or green light. However, the present disclosure is not limited thereto. As the light L emitted from the organic light emitting device OLED, light having a wavelength shorter than the wavelength of light converted by the first to third wavelength converting layers 381, 384, and 387 is sufficient.

In other words, the wavelength of the light emitted from the organic light emitting device OLED may be shorter than 600 nm. However, the present disclosure is not limited thereto.

The wavelength of the light L emitted from the organic light emitting device OLED being shorter than the wavelengths converted by the first to third wavelength converting layers 381, 384, and 387 represents that the energy of the light L emitted from the organic light emitting device OLED is higher than the energy of light converted by the first to third wavelength converting layers 381, 384, and 387.

Since transfer from a high-energy side to a low-energy side has efficiency higher than transfer from a low-energy side to a high-energy side, a light loss can be minimized in the process of converting the wavelength of the light L emitted from the organic light emitting device OLED using the first to third wavelength converting layers 381, 384, and 387.

In addition, the substrate 110 may further include fourth to sixth grooves 324, 325, and 326 in one face in which the first to third grooves 321, 322, 323 are formed.

The fourth groove 324 may be disposed between the first groove 321 and the second groove 322, the fifth groove 325 may be disposed between the second groove 322 and the third groove 323, and the sixth groove 326 may be disposed between the third groove 323 and the first groove 321.

Here, the area of each of the first to third grooves 321, 322, and 323 may be larger than the area of each of the fourth to sixth grooves 324, 325, and 326.

In each of the fourth to sixth grooves 324, 325, and 326, a partition wall may be disposed.

In other words, partition walls 370 may be disposed between the first wavelength converting layer 381 and the second wavelength converting layer 384, between the second wavelength converting layer 384 and the third wavelength converting layer 387, and between the third wavelength converting layer 387 and the first wavelength converting layer 381.

The areas of the first to third wavelength converting layers 381, 384, and 387 disposed inside the first to third grooves 321, 322, and 323 may be larger than the area of the partition wall 370 disposed inside the fourth to sixth grooves 324, 325, and 326.

The partition wall 370 can perform the role of causing light incident to the first to third wavelength converting layers 381, 384, and 387 not to go over another wavelength converting layer adjacent to the wavelength converting layer to which the light has been incident. Accordingly, a light loss according to mutual interference can be minimized.

Such a partition wall 370 may have a refractive index lower than the refractive index of the substrate 110. For example, the refractive index of the substrate 110 may be 1.6 to 1.9, and the refractive index of the partition wall 370 may be equal to or lower than 1.5. However, the present disclosure is not limited thereto.

In this way, by configuring the refractive index of the partition wall 370 to be lower than the refractive index of the first to third wavelength converting layers 381, 384, and 387, light incident in the direction of the partition wall 370 adjacent to the first to third wavelength converting layers 381, 384, and 387 is trapped inside the partition wall 370 and cannot go over another wavelength conversion area adjacent thereto.

With reference to the position of an upper face 110*a* of the substrate 110, an upper face 370*a* of the partition wall 370 may be disposed at a position higher than an upper face 381*a* of the first wavelength converting layer 381, an upper face 384*a* of the second wavelength converting layer 384, and an upper face 387*a* of the third wavelength converting layer 387.

In this way, by disposing the position of the upper face 370*a* of the partition wall 370 at a position higher than the upper face 381*a* of the first wavelength converting layer 381, the upper face 384*a* of the second wavelength converting layer 384, and the upper face 387*a* of the third wavelength converting layer 387, it can be prevented that the materials of the first to third resin layers 382, 385, and 388 and the first to third wavelength converting particles 383, 386, and 389 flow over the partition wall 370 and penetrate into mutually-different wavelength converting layers at the time of manufacturing the first to third wavelength converting layers 381, 384, and 387.

Accordingly, the buffer layer 320 disposed on the substrate 110 may have a sufficient thickness for alleviating a level difference according to the partition wall 370, and a flat layer may be further disposed below or on the buffer layer 320.

In the electronic device 100 according to an aspect of the present disclosure, light L emitted from the organic light emitting device OLED can be extracted to the outside of the electronic device 100 through the buffer layer 320, one of the first to third wavelength converting layers 381, 384, and 387, and the protrusion 311 of the substrate 110.

The refractive indexes of the organic light emitting device OLED, the buffer layer 320, the first to third wavelength converting layers 381, 384, and 387, and the substrate 110 may be associated with each other or similar to each other such that light emitted in the organic layer 350 can be extracted to the outside of the substrate 110 without any loss.

For example, the refractive index of the organic light emitting device OLED may be 1.6 to 1.9, and the refractive index of the substrate 110 may be 1.6 to 1.9, or, as another example, the refractive index of the substrate 110 may be equal to or higher than 1.7. However, the present disclosure is not limited thereto.

In addition, the refractive indexes of the buffer layer 320 and the first to third resin layers 382, 385, and 388 may be 1.6 to 1.9 as well. However, the present disclosure is not limited thereto.

Here, the refractive indexes of the first to third wavelength converting particles 383, 386, and 389 may be set such that an absolute value of a value acquired by subtracting the refractive indexes of the first to third wavelength converting particles 383, 386, 389 from the refractive index of the substrate 110 is a value equal to or smaller than 0.2.

In a case in which the absolute value of a value acquired by subtracting the refractive indexes of the first to third wavelength converting particles 383, 386, 389 from the refractive index of the substrate 110 exceeds 0.2, light provided from the organic light emitting device OLED is not extracted to the outside of the electronic device 100 and may be trapped inside the first to third wavelength converting layers 381, 384, and 387.

The refractive index may be changed in accordance with materials of the first to third wavelength converting particles 383, 386, and 389, and, in a case in which the refractive index of the first to third wavelength converting particles 383, 386, and 389 is higher than the refractive index of the first to third resin layers 382, 385, and 388, the first to third resin layers 382, 385, and 388 may further include scattering particles.

The scattering particles causes the light L emitted from the organic light emitting device OLED to be able to be extracted to the outside of the electronic device 100 without being trapped inside the first to third wavelength converting layers 381, 384, and 387.

In this way, in the electronic device 100 according to an aspect of the present disclosure, light L emitted from organic light emitting device OLED can be easily extracted to the outside of the substrate 110 without being trapped inside the electron device 100.

The substrate 110 may include a plurality of protrusions 311 integrally formed on the rear face for improving light extraction efficiency.

The plurality of protrusions 311 integrally formed on the rear face of the substrate 110 may be provided only one face of the substrate 110. For example, one face of the substrate 110 in which the plurality of protrusions 311 are provided may be one face opposite one face in which the first to third grooves 321, 322, and 323 are formed.

In FIG. 3, although each of the plurality of protrusions 311 is illustrated to have a configuration of a semi-circular shape in a cross-sectional image, the present disclosure is not limited thereto. For example, a sectional shape of each of the plurality of protrusions 311 may be an oval shape or a polygonal shape. In addition, the sectional shapes of at least two protrusions 311 disposed in the active area AA may be different from each other.

The plurality of protrusions 311 can perform the role of inhibiting a phenomenon in which light L emitted from the organic light emitting device OLED is trapped inside the electronic device 100 and is not extracted to the outside of the electronic device 100.

More specifically, light L emitted from the organic light emitting device OLED is directed toward the substrate 110. A face configuring the protrusions 311 formed on the substrate 110 has a slope with respect to a direction in which the substrate 110 extends (horizontal direction).

The slope of the face configuring such protrusions 311 can induce total reflection of light, and light trapped inside the electronic device 100 can be extracted to the outside of the electronic device 100 through this.

The face configuring the plurality of protrusions 311 may have an angle formed with the horizontal plane to be 40 degrees to 60 degrees or an angle formed with the horizontal plane to be 120 degrees to 140 degrees. However, the present disclosure is not limited thereto.

On the other hand, a face configuring the connection part 312 of the substrate 110 may have an angle formed with the horizontal plane not to be 40 degrees to 60 degrees or 120 degrees to 140 degrees.

Accordingly, a probability of occurrence of total reflection of light emitted from organic light emitting device OLED in the connection part 312 of the substrate 110 may be very low. In other words, in an area corresponding to the connection part 312 of the substrate 110, the amount of extracted light may be smaller than in an area corresponding to the protrusions 311 of the substrate 110.

In an area corresponding to the connection part 312, the substrate 110 may have a minimum thickness T1. Here, the thickness of the substrate 110 may be a shortest length with respect to a direction (the vertical direction) in which components of the organic light emitting device OLED are stacked on the surface of the substrate 110.

The connection part 312 of the substrate 110 may overlap with an area in which the insulating film 125 disposed on the substrate 110 is disposed.

In other words, an area in which the substrate 110 has the minimum thickness T1 (in other words, an area corresponding to the connection part) may overlap with the non-light emission area NEA inside the active area AA. In other words, the connection part 312 of the substrate 110 may be disposed between one light emission area EA and another light emission area EA adjacent thereto.

For example, when the connection part 312 is disposed in an area corresponding to the light emission area EA, the connection part 312 is an area that cannot induce total reflection of light emitted from the organic light emitting device OLED, and accordingly, the amount of light extracted to the outside of the substrate 110 may decrease.

Accordingly, one protrusion 311 may correspond to one light emission area EA. However, the present disclosure is not limited thereto, and two or more protrusions 311 may overlap with one light emission area EA depending on the situations.

Meanwhile, in a case in which the electronic device according to an aspect of the present disclosure is a cosmetic device or a treatment device including the organic light emitting device OLED, light emitted from the first to third wavelength conversion areas 281, 282, and 283 may penetrate into the skin of a person.

Since the wavelengths of light emitted from the first to third wavelength converting layers 381, 384, and 387 of the wavelength converting layer 280 are different from each other, depths up to which the light penetrates into the skin may be different.

This will be reviewed as below with reference to FIG. 4.

Figure 4:
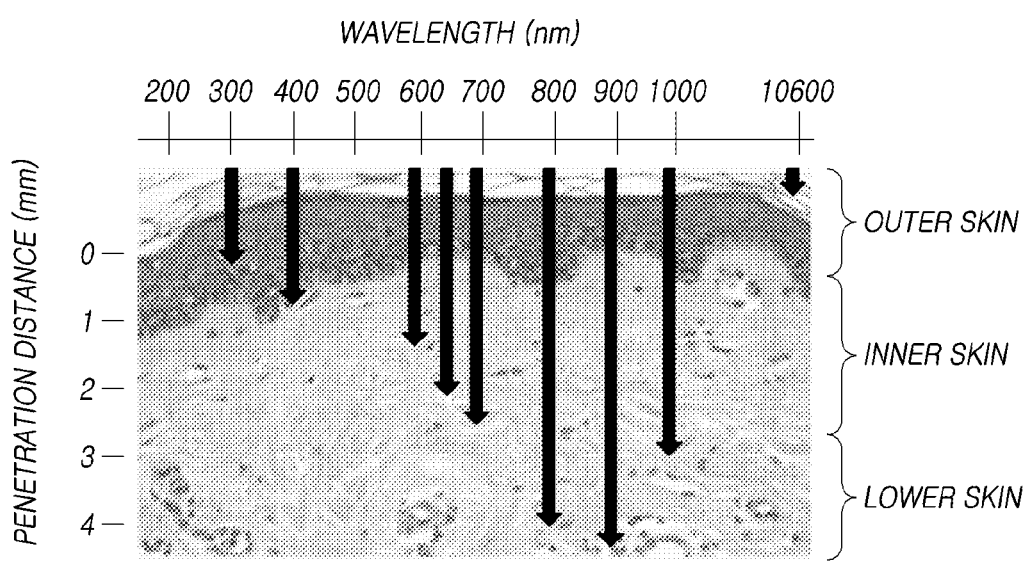
FIG. 4 is a diagram illustrating a penetration depth for a user's skin for each wavelength of light.

FIG. 4 is a diagram illustrating a penetration depth for a user's skin for each wavelength of light.

Referring to FIG. 4, light having a wavelength of about 600 nm to 700 nm can penetrate into outer skin and inner skin of people skin. In addition, light having a wavelength of about 800 nm can penetrate up to outer skin, inner skin, and lower skin (subcutaneous tissues) of people skin.

Light having a wavelength of 630 nm to 830 nm is a main wavelength for acquiring effects of inflammation treatments and skin regeneration through penetration into inner skin and lower skin.

The light extracted to the outside of the electronic device 100 according to an aspect of the present disclosure has a wavelength of 600 nm to 850 nm, and accordingly, in a case in which the electronic device 100 is used as a cosmetic device or a treatment device including an organic light emitting device OLED, remarkable effects can be acquired in the fields of inflammation treatments and skin regeneration.

While the wavelength of effective light is different in accordance with skin thicknesses of ethnic groups and individuals, light extracted from the electronic device 100 according to an aspect of the present disclosure has a broad wavelength band (600 nm to 850 nm), and accordingly, a deviation of effects for inflammation treatments and skin regeneration according to an ethnic group and a skin thickness also can decrease.

In other words, effects of inflammation treatments and skin regeneration can be acquired regardless of a skin thickness that is different for each ethnic group and each user.

In addition, by providing the electronic device 100 emitting light having a wavelength equal to or longer than 780 nm using the organic light emitting device OLED, when the electronic device 100 according to an aspect of the present disclosure is used, skin treatments and skin regeneration can be smoothly performed.

Particularly, while a general cosmetic or treatment device emits only light having a red wavelength band for skin regeneration, the electronic device 100 according to an aspect of the present disclosure emits light having an infrared wavelength band and accordingly, may have an advantage for skin regeneration.

Such an electronic device 100 can be formed through processes as illustrated in FIGS. 5 to 12.

FIGS. 5 to 12 are diagrams schematically illustrating a method of manufacturing an electronic device according to an aspect of the present disclosure.

In the following description, details (configurations, effects, and the like) that are the same as those of the aspects described above may be omitted.

Figure 5:
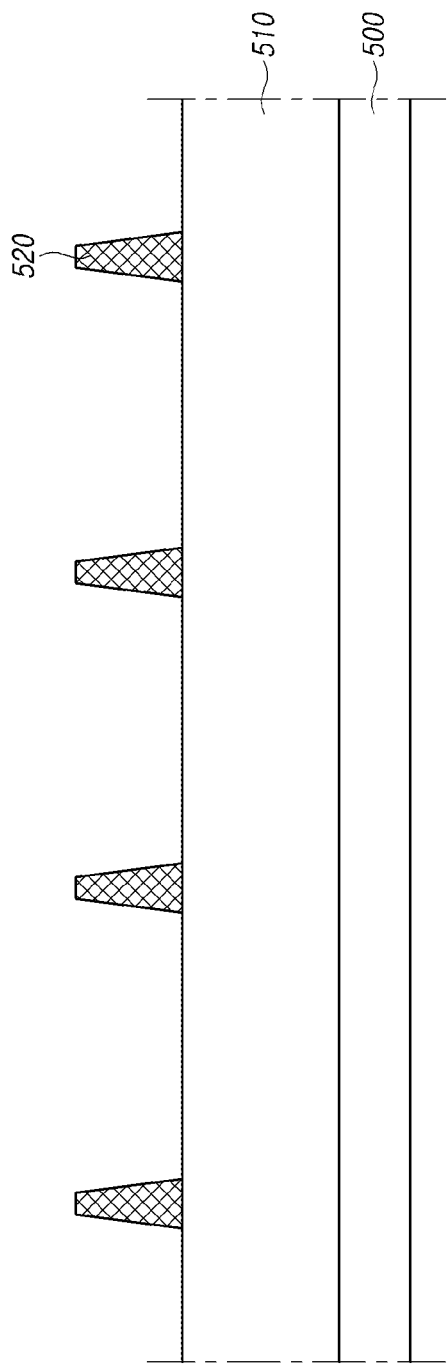
FIGS. 5 to 12 are diagrams schematically illustrating a method of manufacturing an electronic device according to an aspect of the present disclosure.

Referring to FIG. 5, a sacrificial layer 510 may be disposed on a sacrificial substrate 500. A photoresist 520 may be disposed on the sacrificial layer 510.

Here, the sacrificial substrate 500 may be a glass substrate. However, the present disclosure is not limited thereto.

The sacrificial layer 610 may be composed of a material that can be patterned through a photolithography process.

In a state in which the photoresist 520 is disposed illustrated in FIG. 5, the sacrificial layer 610 can be patterned through the photolithography process.

Figure 6:
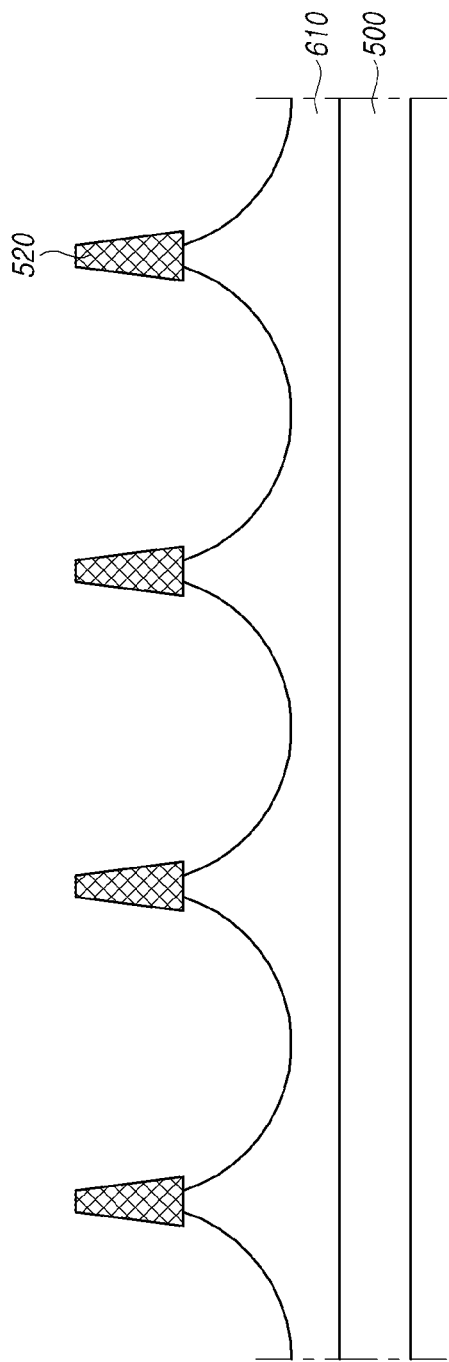
Figure 7:
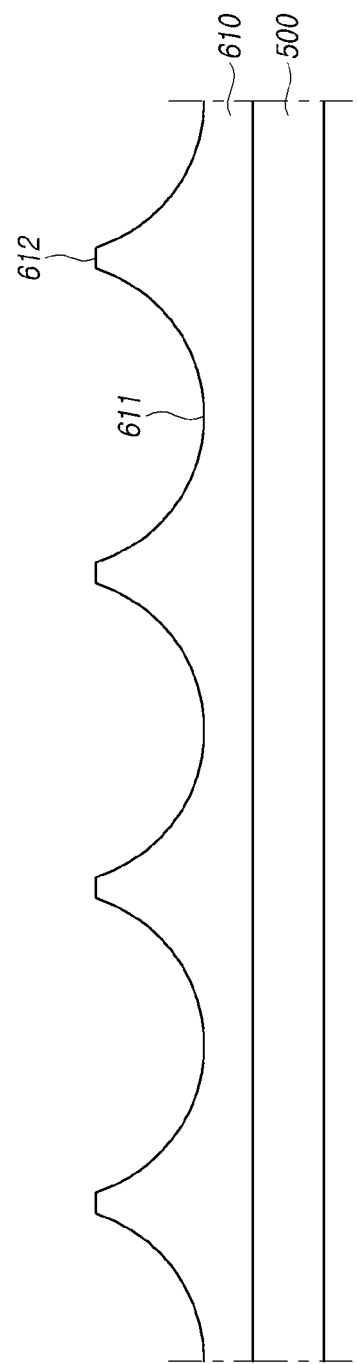

When the sacrificial layer 610 is patterned, as illustrated in FIG. 6, a part of the sacrificial layer 610 in an area in which the photoresist 520 is not disposed may be patterned, and a part of the sacrificial layer 610 in an area in which the photoresist 520 is disposed may not be patterned.

In the sacrificial layer 610 that has been patterned through the photolithography process, a plurality of concave parts 611 and a connection part 612 connecting the plurality of concave parts 611 may be formed.

Figure 8:
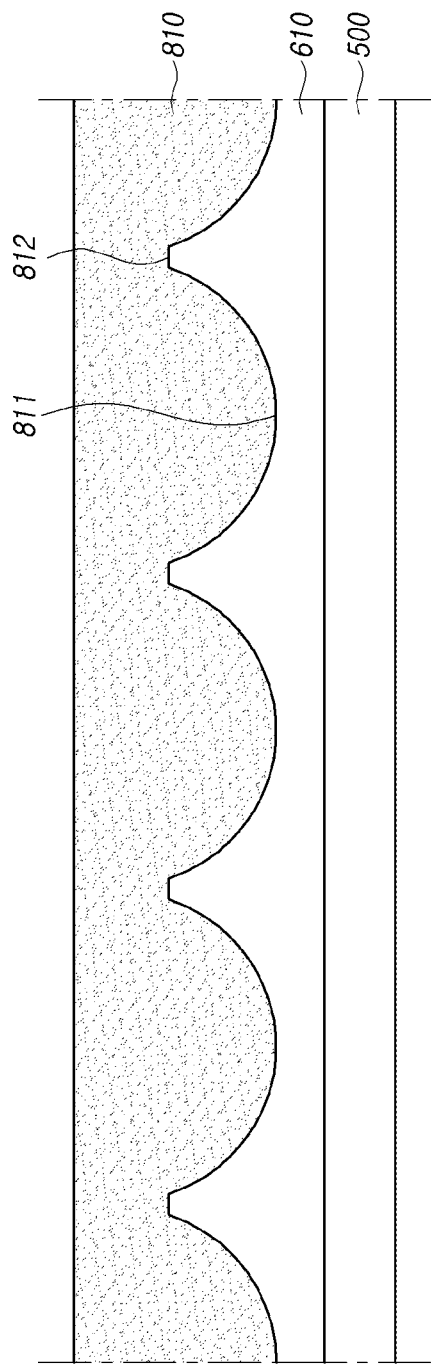

Thereafter, as illustrated in FIG. 8, a substrate layer 810 may be disposed on the sacrificial layer 610.

In a part in which the substrate layer 810 is brought into contact with the sacrificial layer 610, protrusions 811 of the substrate layer 810 may be formed in an area corresponding to the concave parts 611 of the sacrificial layer 610. In an area corresponding to the connection part 612 of the sacrificial layer 610, a connection part 812 of the substrate layer 110 may be formed.

Figure 9:
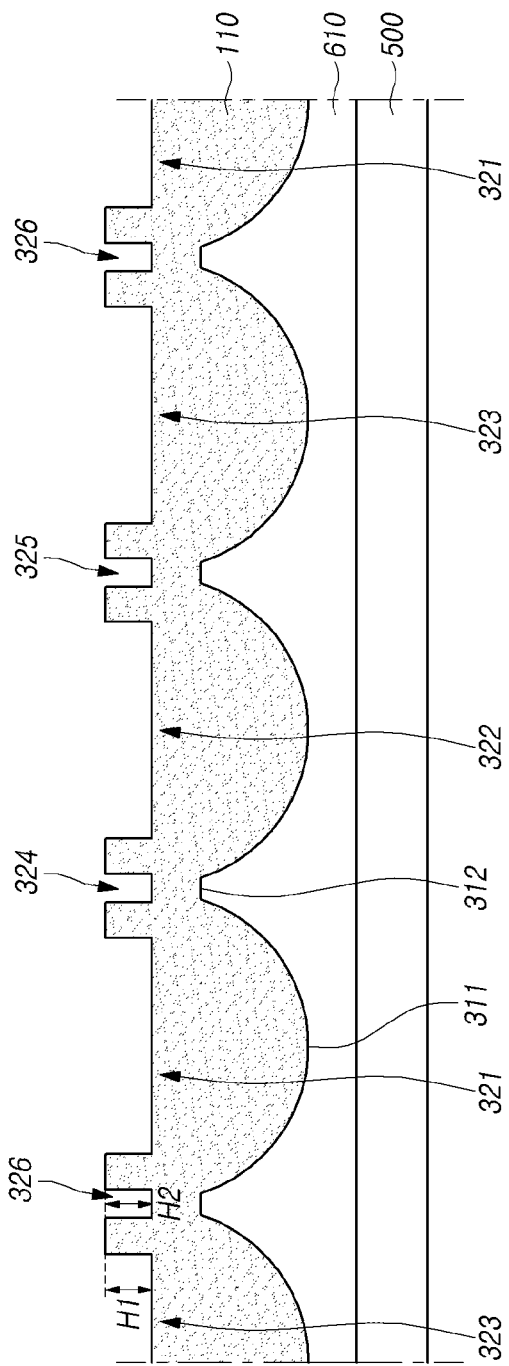

Referring to FIGS. 8 and 9, a plurality of protrusions 811 of the substrate layer 810 may correspond to a plurality of protrusions 311 of the substrate 110 in which the first to sixth grooves 321, 322, 323, 324, 325, and 326 are formed. A plurality of connection parts 812 of the substrate layer 810 may correspond to a plurality of connection parts 312 of the substrate 110 in which the first to sixth grooves 321, 322, 323, 324, 325, and 326 are formed.

On the other face opposite the face of the substrate layer 810 in which the plurality of protrusions 811 and the plurality of connection parts 812 are formed, as illustrated in FIG. 9, first to sixth grooves 321, 322, 323, 324, 325, and 326 are formed.

The first to sixth grooves 321, 322, 323, 324, 325, and 326 may be formed through a photolithography process.

As illustrated in FIG. 9, while a height H1 of the first to third grooves 321, 322, and 323 may correspond to a height H2 of the fourth to sixth grooves 324, 325, and 326, the area of the first to third grooves 321, 322, and 323 may be larger than the area of the fourth to sixth grooves 324, 325, and 326.

Figure 10:
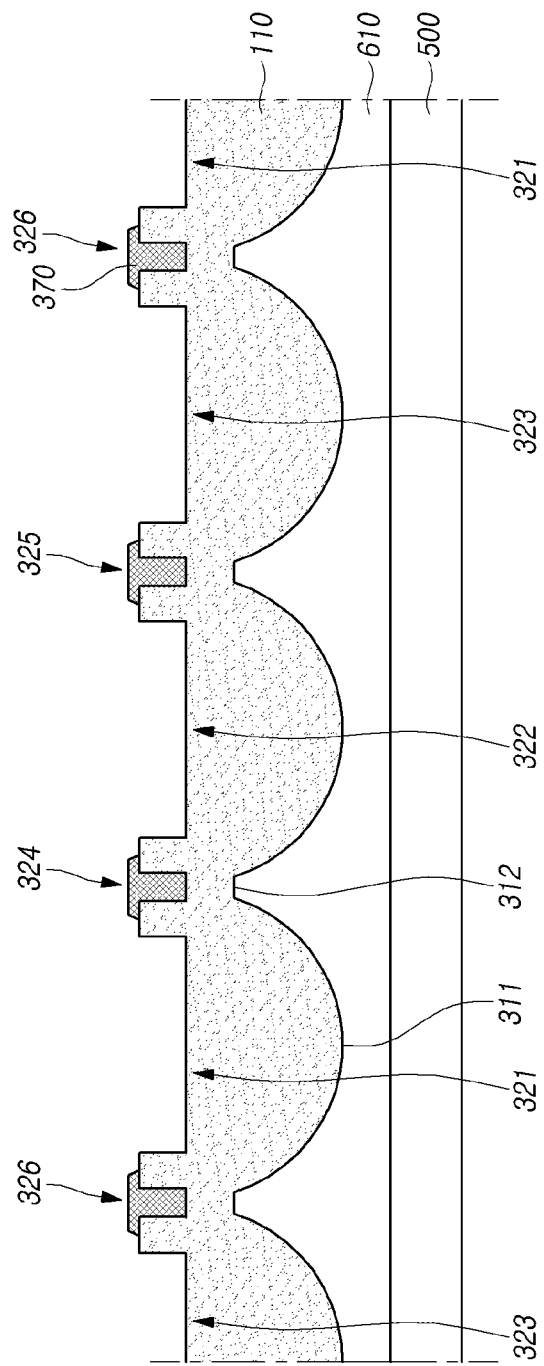

Thereafter, as illustrated in FIG. 10, partition walls 370 may be disposed in the fourth to sixth grooves 324, 325, and 326.

Figure 11:
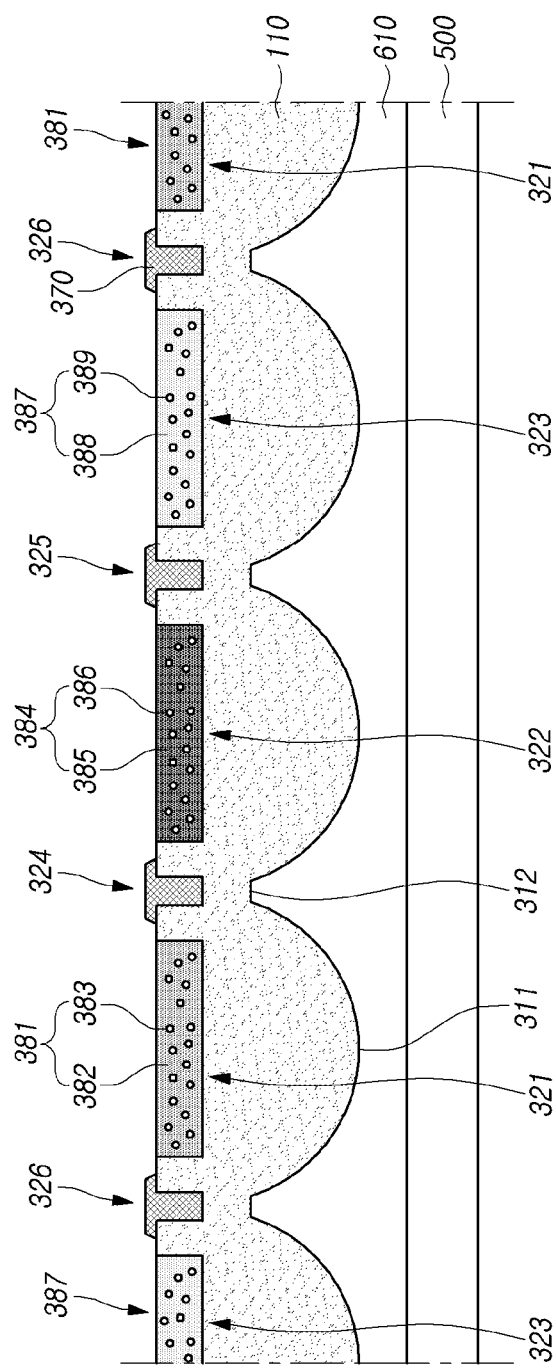

Thereafter, as illustrated in FIG. 11, a first wavelength converting layer 381 is disposed inside the first groove 321, a second wavelength converting layer 384 is disposed inside the second groove 322, and a third wavelength converting layer 387 is disposed inside the third groove 323.

While the first to third wavelength converting layers 381, 384, and 387 may be formed using a coating method, the present disclosure is not limited thereto.

Meanwhile, in order to prevent penetration of each wavelength converting layer material into another wavelength converting layer material at the time of forming the first to third wavelength converting layers 381, 384, and 387, partition walls 370 may be formed before the first to third wavelength converting layers 381, 384, and 387.

Figure 12:
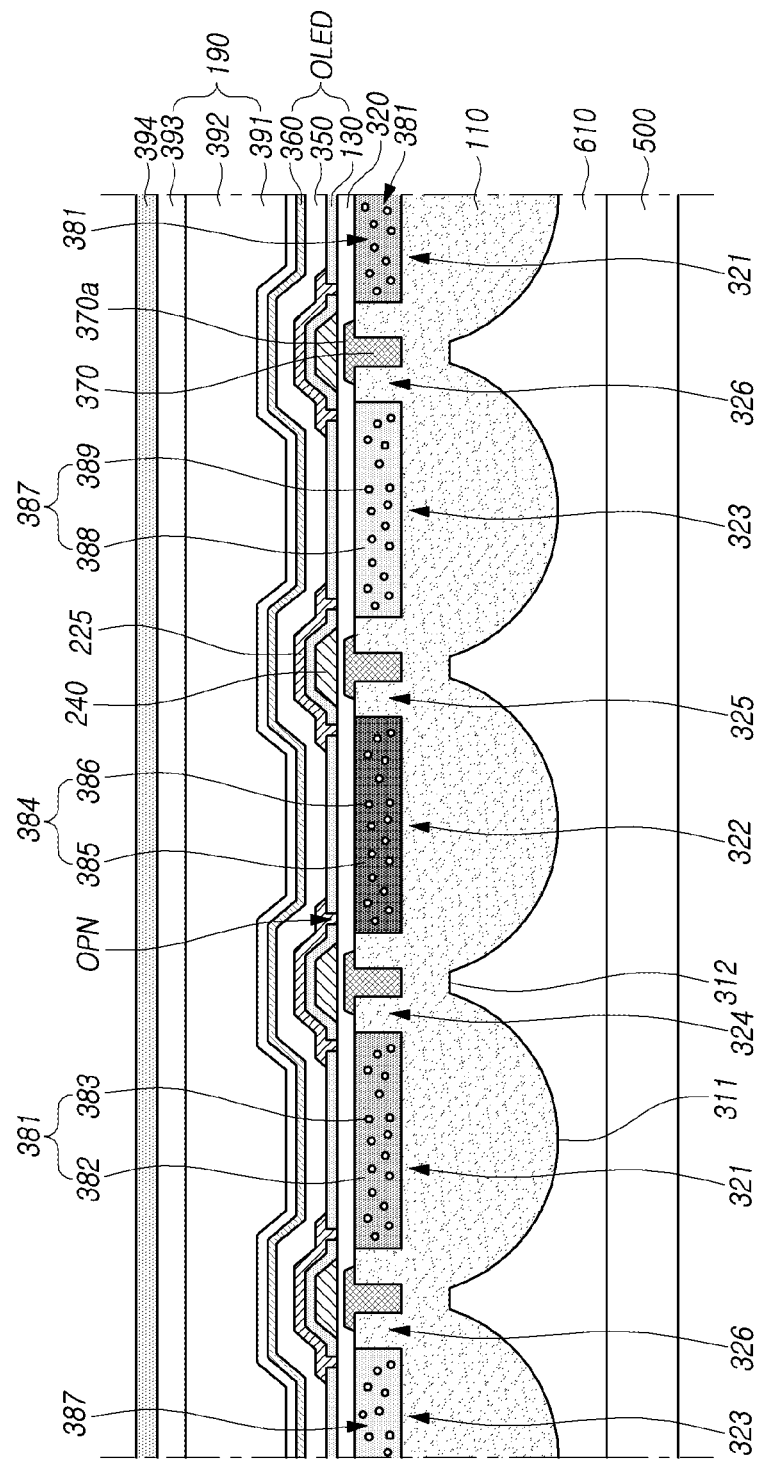

Thereafter, as illustrated in FIG. 12, on the substrate 110 on which the first to third wavelength converting layers 381, 384, and 387 are formed, a buffer layer 320, an auxiliary electrode 240, a first electrode 130, an insulating film 225, an organic layer 350, a second electrode 360, a capping layer 391, a encapsulation layer 392, an adhesion layer 393, and a metal film 394 may be sequentially formed.

Thereafter, the sacrificial layer 610 and the sacrificial substrate 500 may be separated from the substrate 110 through a laser lift off process of emitting laser to the rear face of the substrate 110. However, the process of separating sacrificial layer 610 and the sacrificial substrate 500 from the substrate 110 is not limited thereto.

Such an electronic device 100 may be a cosmetic device or a treatment device including an organic light emitting device OLED. For example, as illustrated in FIG. 13, the electronic device 100 may be a light output device for skin management or a light output device for skin treatments.

Figure 13:
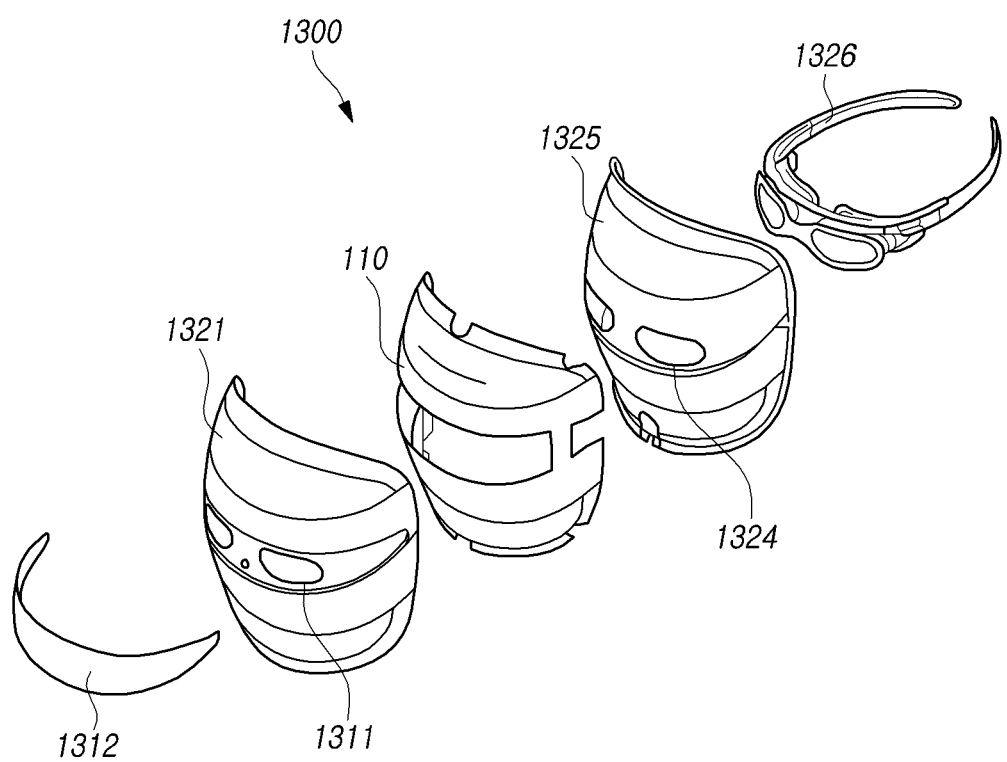
FIG. 13 is a perspective view illustrating the structure of an electronic device according to an aspect of the present disclosure.

FIG. 13 is a perspective view illustrating the structure of an electronic device according to an aspect of the present disclosure.

In the following description, details (configurations, effects, and the like) that are the same as those of the aspects described above may be omitted.

Referring to FIG. 13, an electronic device 1300 according to an aspect of the present disclosure may include a front cover 1321, a substrate 110, a rear cover 1325, and a wearing device 1326.

The front cover 1321 is disposed on the front face of the electronic device 1300 and can protect the substrate 110 disposed between the rear cover 1325 and the front cover 1321 from an external shock, a contact, and the like. For this, the front cover 1321 may be realized using various kinds of plastic, ceramics, and the like. However, the present disclosure is not limited thereto.

In the front cover 1321, an opening 1311 used for securing the field of vision of a user when being worn by the user may be formed. When a user wears the electronic device 1300, the eyes of the user are positioned in the opening 1311, and the user can secure the field of vision through the opening 1311.

In order to prevent a contact or collision of a foreign material with the eyes of the user through the opening 1311, an opening protection cover 1312 covering the opening 1311 may be provided depending on the situations. The opening protection cover 1312 may be realized using a transparent material such as acryl or plastic. However, the present disclosure is not limited thereto.

In the substrate 110, as illustrated in FIG. 3, a plurality of protrusions 311 may be integrally formed one face, and first to third wavelength converting layers 381, 384, and 387 and partition walls 370 may be formed on the other face. Then, auxiliary electrodes 240, an insulating film 225, an organic light emitting device OLED, and an encapsulation member 390 may be disposed on the first to third wavelength converting layers 381, 384, and 387 and the partition walls 370.

Although not illustrated in the drawing, the substrate 110 may include a control unit used for controlling a light output operation of at least one light source. The control unit may be realized by an integrated circuit (IC), a microcomputer, an embedded processor, an application processor (AP), or the like. The control unit may be included in a user operation device to be described later in accordance with an aspect.

In addition, the substrate 110 included in the electronic device 1300 having a mask shape may be formed such that at least a part thereof forms a curved face.

The rear cover 1325 is fastened to the front cover 1321 and the substrate 110 and may be formed to cover one face of the substrate 110. The front cover 1321 and the rear cover 1325 prevent penetration of water and other foreign materials to the substrate 110 disposed inside thereof and can prevent malfunctions and damages in a light source and other constituent elements disposed in the substrate 110.

In order to allow light emitted from the light source disposed in the substrate 110 to be emitted to a user's facial skin, the rear cover 1325 may be realized using a transparent material such as plastic or acryl. In addition, the rear cover 1325 may include an opening 1324 used for securing the field of view of a user.

The wearing device 1326 can fix the electronic device 1300 to a user as the user wears the electronic device 1300. The wearing device 1326 may be fastened to the rear cover 1325. For example, the wearing device 1326 may have a glass shape that can be worn by being settled in the nose and the ears of the user.

Since light extracted to the outside of the electronic device 1300 can be configured to have a wavelength of 600 nm to 850 nm, remarkable effects can be acquired in the fields of inflammation treatments and skin regeneration.

In addition, since light extracted from the electronic device 1300 according to an aspect of the present disclosure has a broad wavelength band (600 nm to 850 nm), deviations in the effects of inflammation treatments and skin regeneration according to an ethnic group and a skin thickness can be decreased.

The above description and the accompanying drawings provide an example of the technical idea of the present disclosure for illustrative purposes only. Those having ordinary knowledge in the technical field, to which the present disclosure pertains, will appreciate that various modifications and changes in form, such as combination, separation, substitution, and change of a configuration, are possible without departing from the essential features of the present disclosure. Therefore, the aspects disclosed in the present disclosure are intended to illustrate the scope of the technical idea of the present disclosure, and the scope of the present disclosure is not limited by the aspect. The scope of the present disclosure shall be construed on the basis of the accompanying claims in such a manner that all of the technical ideas included within the scope equivalent to the claims belong to the present disclosure.

What is claimed is:

1. An electronic device for skin management or skin treatments including an active area including a light emission area and a non-light emission area, the electronic device comprising:
    a plurality of organic light emitting devices including a first electrode disposed on a substrate, an organic layer disposed on the first electrode and a second electrode disposed on the organic layer, and disposed in the light emission area and emitting same color light;
    first to third wavelength converting layers overlapping the light emission area and a part of the non-light emission area, and
    a partition wall disposed in the substrate and separating the first to third wavelength converting layers from each other,
    wherein each of the first to third wavelength converting layers includes a resin layer and a plurality of wavelength converting particles dispersed in the resin layer,
    wherein light emitted from the plurality of organic light emitting devices is extracted to outside the electronic device through the first to third wavelength converting layers,
    wherein the partition wall has a refractive index lower than those of the substrate and the first to third wavelength converting layers.

2. The electronic device according to claim 1,
    wherein the first to third wavelength converting layers are disposed in the substrate.

3. The electronic device according to claim 1, wherein the organic light emitting devices are configured to emit green color light or blue color light.

4. The electronic device according to claim 2, wherein the first electrode includes a transparent conductive material and the second electrode includes a reflective metal.

5. The electronic device according to claim 2, wherein the organic layer includes at least a light emitting layer, and
    wherein a wavelength of light emitted from the organic layer is smaller than a wavelength converted by the first to third wavelength converting layers.

6. The electronic device according to claim 1, wherein light emitted through the first to third wavelength converting layers has a wavelength ranging from 600 nm to 850 nm.

7. The electronic device according to claim 1, wherein light emitted through the first to third wavelength converting layers includes light for penetrating into outer skin and inner skin of a user's skin, and light for penetration into inner skin and lower skin of the user's skin,
    wherein the inner skin is disposed between the outer skin and the lower skin.

8. The electronic device according to claim 2, wherein the first wavelength converting layer, the second wavelength converting layer, and the third wavelength converting layer convert light emitted from the organic layer into different wavelengths.

9. The electronic device according to claim 8, wherein at least one of the first to third wavelength converting layers converts the light emitted from the organic light emitting device into an infrared wavelength band.

10. The electronic device according to claim 1, wherein each of the first wavelength converting layer, the second wavelength converting layer and the third wavelength converting layer includes a resin layer and a plurality of wavelength converting particles dispersed in the resin layer.

11. The electronic device according to claim 2, wherein the substrate includes a first groove, a second groove, and a third grove that overlap the light emission area and a part of the non-light emission area and are separate from each other are formed in one face of the substrate disposed the first electrode, and
    wherein the first wavelength converting layer is disposed inside the first groove, the second wavelength converting layer is disposed inside the second groove, and the third wavelength converting layer is disposed inside the third groove.

12. The electronic device according to claim 11, wherein the substrate further includes a fourth groove disposed between the first groove and the second groove, a fifth groove disposed between the second groove and the third groove, and a sixth groove disposed between the third groove and the first groove.

13. The electronic device according to claim 12, wherein each of the first to third grooves is larger than each of the fourth to sixth grooves.

14. The electronic device according to claim 12, further comprising a partition wall disposed inside the fourth to sixth grooves.

15. The electronic device according to claim 14, wherein an upper face of the partition wall is disposed at a position higher than upper faces of the first to third wavelength converting layers with respect to a position of an upper face of the substrate.

16. The electronic device according to claim 2, further comprising:
    an auxiliary electrode having a mesh shape and disposed on the substrate, a part of the first electrode overlapping an open area of the auxiliary electrode and a part of the first electrode connecting with the auxiliary electrode and including at least one open area in an area not overlapping the auxiliary electrode; and
    an insulating film that overlaps the auxiliary electrode, overlaps another part of the first electrode and disposed to cover the open area of the first electrode.

17. The electronic device according to claim 16, wherein, in the active area, the non-light emission area corresponds to an area in which the insulating film is disposed, and the light emission area corresponds to an area in which the insulating film is not disposed.

18. The electronic device according to claim 16, wherein the first electrode has a resistivity higher than that of the auxiliary electrode.

19. The electronic device according to claim 14, further comprising:
    an auxiliary electrode having a mesh shape and disposed on the substrate, the first electrode overlapping an open area of the auxiliary electrode and a part of the first electrode connecting with the auxiliary electrode including at least one open area in an area not overlapping with the auxiliary electrode; and
    an insulating film that overlaps the auxiliary electrode, overlaps a part of the first electrode and disposed to cover the open area of the first electrode.

20. The electronic device according to claim 19, wherein the partition wall overlaps the insulating film.

21. The electronic device according to claim 2, wherein the substrate has a first side in which a plurality of protrusions are integrally formed, and the first to third wavelength converting layers are formed in a second side of the substrate opposite the first side and facing the first electrode.

22. The electronic device according to claim 21, further comprising:
- an auxiliary electrode having a mesh shape and disposed on the substrate, the first electrode overlapping an open area of the auxiliary electrode and a part of the first electrode connecting with the auxiliary electrode including at least one open area in an area not overlapping with the auxiliary electrode; and
- an insulating film that overlaps the auxiliary electrode, overlaps a part of the first electrode and disposed to cover the open area of the first electrode.

23. The electronic device according to claim 22, wherein the substrate has a minimum thickness between two adjacent protrusions, and
- wherein at least one area in which the substrate has the minimum thickness overlaps the insulating film and the partition wall.

24. The electronic device according to claim 2, further comprising an encapsulation member disposed on the second electrode,
- wherein the encapsulation member includes:
- a capping layer disposed to cover the second electrode;
- an encapsulation layer disposed to cover the capping layer;
- an adhesion layer disposed on the substrate on which the encapsulation layer is disposed; and
- a metal film disposed on the adhesion layer.

* * * * *